United States Patent
Xu et al.

(10) Patent No.: US 10,434,233 B2
(45) Date of Patent: Oct. 8, 2019

(54) BLOOD PUMP CONTROL SYSTEM AND BLOOD PUMP SYSTEM

(71) Applicants: BEIJING RESEARCH INSTITUTE OF PRECISE MECHATRONICS AND CONTROLS, Beijing (CN); ROCKETHEART TECHNOLOGY CO. LTD., Tianjin (CN)

(72) Inventors: Jian Xu, Beijing (CN); Jipeng Li, Beijing (CN); Wei Wang, Beijing (CN); Jingjing Su, Beijing (CN); Xue Li, Beijing (CN); Lei Zhang, Beijing (CN)

(73) Assignees: Beijing Research Institute of Precise Mechatronics and Controls, Beijing (CN); RocketHeart Technology Co. LTD, Tianjin (CN)

( * ) Notice: Subject to any disclaimer, the term of this patent is extended or adjusted under 35 U.S.C. 154(b) by 699 days.

(21) Appl. No.: 14/410,177

(22) PCT Filed: Nov. 27, 2013

(86) PCT No.: PCT/CN2013/001454
§ 371 (c)(1),
(2) Date: Dec. 22, 2014

(87) PCT Pub. No.: WO2015/048920
PCT Pub. Date: Apr. 9, 2015

(65) Prior Publication Data
US 2016/0263299 A1  Sep. 15, 2016

(30) Foreign Application Priority Data
Oct. 3, 2013 (CN) .......................... 2013 1 0462858

(51) Int. Cl.
*A61M 1/10* (2006.01)
*A61M 1/12* (2006.01)

(52) U.S. Cl.
CPC ........ *A61M 1/1086* (2013.01); *A61M 1/1031* (2014.02); *A61M 1/101* (2013.01);
(Continued)

(58) Field of Classification Search
CPC .............. A61M 1/1086; A61M 1/1031; A61M 2205/3584; A61M 2205/3553; A61M 2205/18; A61M 2230/005
See application file for complete search history.

(56) References Cited

U.S. PATENT DOCUMENTS 5,959,529 A * 9/1999 Kail, IV .................. G01S 19/17
128/903
7,794,384 B2 * 9/2010 Sugiura ............... A61M 1/1086
600/16
(Continued)

FOREIGN PATENT DOCUMENTS

CN 101056663 A 10/2007
CN 101983732 A 3/2011
(Continued)

*Primary Examiner* — Alyssa M Alter
(74) *Attorney, Agent, or Firm* — Laurence A. Greenberg; Werner H. Stemer; Ralph E. Locher

(57) ABSTRACT

A blood pump control system includes a local processing terminal and a remote processing terminal. The local processing terminal is configured to transmit to the remote processing terminal, collected current state parameters of the blood pump and heart activity indexes, and to drive and control the blood pump according to blood pump adjusting parameters received from the remote processing terminal. The remote processing terminal is configured to obtain current blood pump adjusting parameters according to the current state parameters, and the heart activity indexes received from the local processing terminal, and set adjusting conditions; and to transmit the blood pump adjusting parameters back to the local processing terminal.

19 Claims, 6 Drawing Sheets

(52) U.S. Cl.
CPC ......... *A61M 1/122* (2014.02); *A61M 2205/18* (2013.01); *A61M 2205/3334* (2013.01); *A61M 2205/3507* (2013.01); *A61M 2205/3553* (2013.01); *A61M 2205/3561* (2013.01); *A61M 2205/3569* (2013.01); *A61M 2205/3584* (2013.01); *A61M 2230/005* (2013.01); *A61M 2230/04* (2013.01)

(56) References Cited

U.S. PATENT DOCUMENTS

| | | |
|---|---|---|
| 8,610,583 B2 | 12/2013 | Sasaki |
| 8,764,621 B2 | 7/2014 | Badstibner et al. |
| 2009/0149950 A1 | 6/2009 | Wampler |
| 2009/0226328 A1 | 9/2009 | Morello |
| 2010/0036487 A1 | 2/2010 | Crosby et al. |
| 2010/0130809 A1 | 5/2010 | Morello |
| 2010/0135832 A1 | 6/2010 | Wampler et al. |

FOREIGN PATENT DOCUMENTS

| | | |
|---|---|---|
| CN | 102046221 A | 5/2011 |
| CN | 203507200 U | 4/2014 |
| WO | 2008124696 A1 | 10/2008 |
| WO | 2013009881 A2 | 1/2013 |

\* cited by examiner dynamically modifies related parameters of the blood pump according to monitoring of current state parameters of the blood pump, to thereby realize a closed loop control of blood pump adjusting parameters.

BLOOD PUMP CONTROL SYSTEM AND BLOOD PUMP SYSTEM

BACKGROUND OF THE INVENTION

Field of the Invention

The present invention relates to medical appliances, and in particular to a blood pump control system, a blood pump control method and a blood pump system.

Chronic Heart Failure (CHF) increasingly becomes one of the most common and harmful diseases in cardiovascular diseases, and is the same end-stage performance of many types of cardiovascular diseases. It is estimated according to statistical data on population and morbidity, there are more than 80,000,000 heart failure patients in the world and there are more than 16,000,000 patients in China. With the increasing growing of advanced aging of the Chinese population, the number of heart failure patients is increasing in China year by year. As to end-stage heart failure, its traditional therapeutic effect is poor and mid-term and long-term mortality rate is high, and since donors for effective heart transplantation are in short supply, a lot of heart failure patients die in waiting for heart transplantation. End-stage heart failure treatment and nursing consume a huge amount of resources and have already become social, medical and health problems in the world.

Artificial assist heart (simply referred to as blood pump) is a most effective therapeutic instrument of all kinds of end-stage heart failures, recognized in the world. In general, an inflow cannula of the blood pump is communicated with a left ventricle or right ventricle of people's heart, and an outflow graft of the blood pump is communicated with an aorta or pulmonary artery, and the blood pump is connected to a control driver (provided with a power supply device) that controls the blood pump to output blood with a certain pressure (generally 80~120 mmHg) and flow (generally 2~10 L/min) to share the responsibility of power requirements of body normal activities on the heart. According to the position of heart chambers assisted by the blood pump, there are left ventricle assist device (LVAD), right ventricle assist device (RVAD), and bi-ventricle assist device (Bi-VAD). Artificial assist heart can not only serve as short-term assistance in acute heart failure, chronic heart failure acute attack and low cardiac output after heart operations, but also serve as a bridge prior to heart transplantation and destination therapy of end-stage heart failure instead of heart transplantation. After years of research, artificial assist heart had developed from first-generation pulsatile blood pump, second-generation axial rotary blood pump to third-generation suspending rotary blood pump. Most of the third-generation suspending rotary blood pumps control impeller rotation speed in an open loop mode, that is, it is only set that the blood pump operates with a constant rotation speed without taking a change in physiological parameters of the patient into consideration. Therefore, when the physiological condition of the patient changes, the blood pump is apt to operate abnormally, resulting in a poor assisting effect and reduced reliability.

BRIEF SUMMARY OF THE INVENTION

In view of the above defects in the prior art, an aspect of the invention provides a blood pump control system and a blood pump system, and another aspect of the invention provides a blood pump control method that remotely dynamically modifies related parameters of the blood pump The blood pump control system according to an embodiment of the invention comprises: a local processing terminal and a remote processing terminal;

wherein the local processing terminal is configured to transmit to the remote processing terminal, collected current state parameters of the blood pump and heart activity indexes; and to drive and control the blood pump according to blood pump adjusting parameters received from the remote processing terminal; and wherein the remote processing terminal is configured to obtain current blood pump adjusting parameters according to the current state parameters and the heart activity indexes received from the local processing terminal, and the set adjusting conditions; and to transmit the blood pump adjusting parameters back to the local processing terminal.

In some embodiments, the local processing terminal comprises: a collecting module, a remote transmitting terminal and a driving module, wherein the collecting module is configured to collect blood pump state parameters and heart activity indexes of a carrier;

wherein the remote transmitting terminal is configured to transmit the blood pump state parameters and the heart activity indexes of the carrier to the remote processing terminal in a wireless or wired communication mode;

wherein the collecting module is connected to the remote transmitting terminal via USB and/or a short distance wireless communication interface;

wherein the driving module is configured to drive and control the blood pump according to the blood pump adjusting parameters received from the remote processing terminal.

In some embodiments, a power supply of the local processing terminal comprises a direct current (DC) power supply and/or an alternating current (AC) power supply.

In some embodiments, the local processing terminal further comprises: a local low-electricity warning module configured to generate local low-electricity warning information or a low-electricity warning acknowledgement request if a total electricity or voltage value of the DC power supply and AC power supply is lower than a set electricity or voltage value.

In some embodiments, the local low-electricity warning module is further configured to generate remote low-electricity warning information if a warning acknowledgement is not received within a set period.

In some embodiments, the local processing terminal further comprises: a local pump state warning module configured to generate local pump state warning information or a pump state warning acknowledgement request if a first motor feedback signal or second motor feedback signal of the blood pump is an abnormal signal.

In some embodiments, the local pump state warning module is further configured to generate remote pump state warning information if a warning acknowledgement is not received within a set period.

In some embodiments, the local processing terminal further comprises a local state parameter warning module configured to generate local state parameter warning information or a state parameter warning acknowledgement request if any value of pump voltage, pump current, pump rotation speed, pump flow and heart rate is abnormal.

In some embodiments, the local state parameter warning module is further configured to generate remote state parameter warning information if a warning acknowledgement is not received within a set period.

In some embodiments, the local processing terminal further comprises: a warning device configured to output the local low-electricity warning information, the local pump state warning information and/or the local state parameter warning information.

In some embodiments, the remote transmitting terminal is further configured to transmit the remote low-electricity warning information, the remote pump state warning information or the remote state parameter warning information to the remote processing terminal in a wireless or wired communication mode.

In some embodiments, the remote transmitting terminal further comprises a GPS navigation module configured to obtain current position navigation information if the remote low-electricity warning information, the remote pump state warning information or the remote state parameter warning information is received.

In some embodiments, the remote transmitting terminal is further configured to make a call request to a first emergency call number via a local number, if the remote low-electricity warning information, the remote pump state warning information or the remote state parameter warning information is received; and to make a call request to a second emergency call number if the first emergency call number does not reply within a set period.

In some embodiments, the remote transmitting terminal is further configured to generate low-electricity warning instant information, pump state warning instant information or state parameter warning instant information according to the remote low-electricity warning information, the remote pump state warning information or the remote state parameter warning information, if the remote low-electricity warning information, the remote pump state warning information or the remote state parameter warning information is received; to transmit the low-electricity warning instant information, the pump state warning instant information or the state parameter warning instant information to a first emergency call number via a local number; and to transmit the low-electricity warning instant information, the pump state warning instant information or the state parameter warning instant information to a second emergency call number if a reply to the instant information is not received within a set period.

In some embodiments, the remote transmitting terminal is further configured to generate low-electricity warning instant information, pump state warning instant information or state parameter warning instant information according to the remote low-electricity warning information, the remote pump state warning information or the remote state parameter warning information and the position navigation information, if the remote low-electricity warning information, the remote pump state warning information or the remote state parameter warning information is received; to transmit the low-electricity warning instant information, the pump state warning instant information or the state parameter warning instant information to a first emergency call number via a local number; and to transmit the low-electricity warning instant information, the pump state warning instant information or the state parameter warning instant information to a second emergency call number if a reply to the instant information is not received within a set period.

In some embodiments, the remote processing terminal comprises a remote service platform and a remote processing platform, wherein the remote service platform is configured to receive the current pump voltage, pump current, pump rotation speed, pump flow, heart rate from the local processing terminal; and to transmit the blood pump adjusting parameters obtained by the remote processing platform back to the local processing terminal; and the remote processing platform is configured to obtain current blood pump adjusting parameters according to the current pump voltage, pump current, pump rotation speed, pump flow, heart rate, history heart activity indexes of the patient, and the set adjusting conditions.

In some embodiments, the remote processing platform comprises a first remote processing platform and a second remote processing platform, wherein an authority of the current blood pump adjusting parameters obtained by the first remote processing platform is higher than an authority of the current blood pump adjusting parameters obtained by the second remote processing platform.

In some embodiments, the remote processing terminal further comprises: a warning transmitting module configured to generate low-electricity warning push information, pump state warning push information or state parameter warning push information according to the low-electricity warning information and its corresponding position navigation information, the pump state warning information and its corresponding position navigation information or the state parameter warning information and its corresponding position navigation information.

In some embodiments, the warning transmitting module is further configured to transmit an instant message to a first emergency number according to the remote low-electricity warning push information, the remote pump state warning push information or the remote state parameter warning push information or push the information to a first emergency account, if the remote low-electricity warning push information, the remote pump state warning push information or the remote state parameter warning push information is received; and to transmit an instant message to a second emergency number or push the information to a second emergency account if a reply from the first emergency call number is not received within a set period.

In some embodiments, the local processing terminal further comprises: a remote receiving terminal configured to receive the current blood pump adjusting parameters from the remote processing terminal in a wireless or wired communication mode, wherein the wireless communication mode can be wifi, 2G/3G.

The invention also provides a blood pump control method comprising following steps:

transmitting, by a local processing terminal, collected current state parameters of the blood pump and heart activity indexes, to a remote processing terminal;

obtaining, by the remote processing terminal, current blood pump adjusting parameters, according to the current state parameters and the heart activity indexes received from the local processing terminal, and set adjusting conditions; and transmitting the blood pump adjusting parameters back to the local processing terminal;

driving and controlling, by the local processing terminal, the blood pump according to the blood pump adjusting parameters received from the remote processing terminal.

The invention also provides a blood pump system comprising a blood pump and the above-mentioned blood pump control system.

As compared with the prior art, the blood pump control system and blood pump system according to the invention have the following advantages: the invention uploads, in a wired or wireless mode, operating state information such as collected voltage, current, rotation speed of the blood pump carried by the carrier to the remote server that on the one hand stores the data in a database to enrich samples for subsequent optimization, and on the other hand adjusts blood pump operating parameters according to judgments made by specified doctors and nurses or device manufacturers according to the patent's data, such that the blood pump is more adapted to use by the carrier to improve reliability and security of the use of the blood pump.

DESCRIPTION OF THE INVENTION

The invention is further described in detail below in combination with the accompanying drawings, but the detailed descriptions cannot be construed as limiting the invention in anyway.

Figure 1:
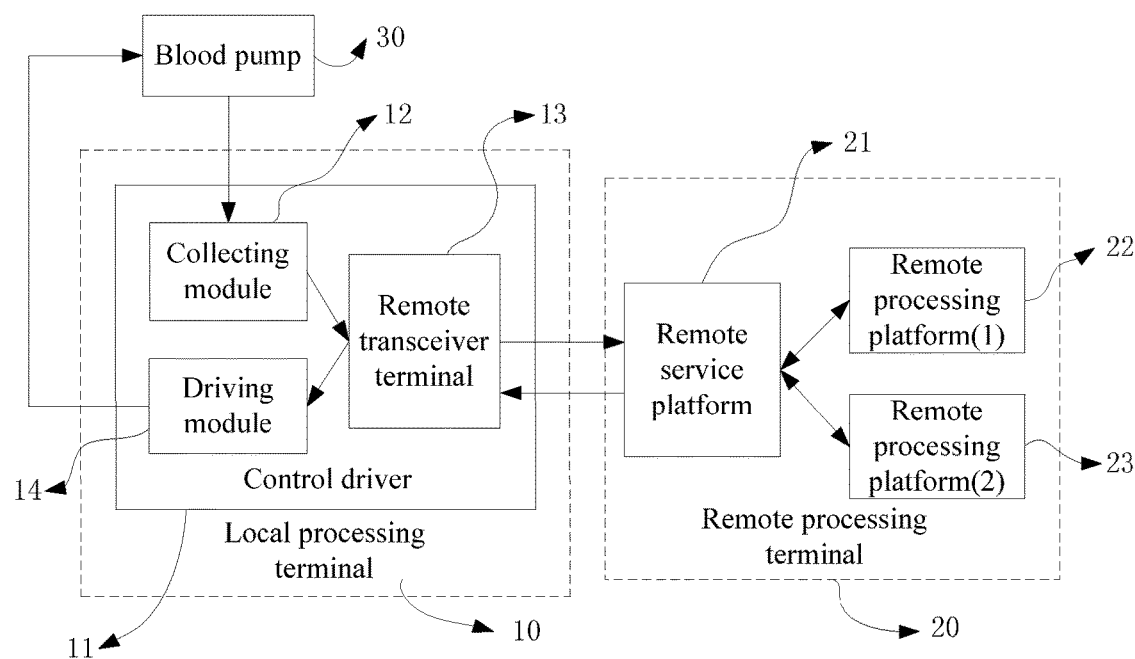
FIG. 1 is a schematic diagram showing components of a blood pump control system according to an embodiment of the invention.

As shown in FIG. 1, a local processing terminal 10 of the blood pump control system according to an embodiment of the invention comprises: a control driver 11 that may be implemented by an embedded system using a DSP processor. A remote processing terminal 20 comprises a remote service platform 21, a remote processing platform (1) 22 and/or a remote processing platform (2) 23. For monitoring a state of a carrier, basic information of the carrier, e.g., carrier identity (unique identification for identifying a user), name, age, disease history, time to use the blood pump 30 initially, shall be unified and maintained consistent in both the local processing terminal 10 and the remote processing terminal 20. The control driver 11 comprises a collecting module 12, a remote transceiver terminal 13 and a driving module 14. The collecting module 12 is connected to the blood pump 30 to be monitored via a percutaneous wire passing through human body's abdomen, to collect current state parameters of the blood pump 30 and heart activity indexes of the carrier, wherein the current state parameters comprise: pump voltage, pump current, pump rotation speed, pump flow; and heart activity indexes of the carrier comprise: physiological indexes such as heart rate. The collecting module 12 is connected to the remote transceiver terminal 13 via USB and/or short distance wireless communication interface, to transmit the collected current state parameters and the heart activity indexes of the carrier to the remote transceiver terminal 13 via USB and/or short distance wireless communication mode, wherein the short distance wireless communication mode can use Bluetooth communication or the like. The remote transceiver terminal 13 transmits "current state parameters and heart activity indexes of the carrier" to the remote service platform 21 of the remote processing terminal 20 in a wireless or wired communication mode, wherein the wireless communication mode can be wifi, 2G/3G. It should be noted that, the remote transceiver terminal 13 can be integrated into the control driver 11 as needed. If the remote transceiver terminal 13 is integrated into the control driver 11, the remote transceiver terminal 13 can be divided into a "remote transmitting module" and a "remote receiving module", which has an advantage that the collecting module 12 and the remote transceiver terminal 13 can be directly connected to one another via a line to improve reliability of the system. Furthermore, the remote transceiver terminal 13 can also be implemented using a mobile phone terminal or a smart phone mobile terminal independent of the control driver 11, which has an advantage of facilitating the user to carry it. The remote service platform 21 can be implemented via a remote information server.

After the remote service platform 21 receives the parameters and the indexes from the local processing terminal 10, it notifies the remote processing platform (1) 22 monitored by a medical unit and the remote processing platform (2) 23 monitored by a blood pump provider, or notifies any one of the remote processing platform (1) 22 and the remote processing platform (2) 23. Firstly, the carrier and its history information are retrieved from a server platform database according to the current carrier identity of the blood pump 30. Thereafter driving parameters such as current blood pump revolution of the carrier are set according to the set adjusting conditions in combination with the history information and the current state parameters (pump voltage, pump current, pump rotation speed, pump flow) and the heart activity indexes (heart rate) of the carrier. For example, the time to initially wear the pump by the carrier is Jan. 10, 2010, the current collecting time is Jan. 10, 2011, the heart rate when the carrier worn it initially is 80 times/minute, voltage is 14V, current is 0.3 A, initial revolution is 2400 rpm, and corresponding pump assisting flow is 3 L/min. If the currently collected heart rate of the carrier maintains 80 times/minute, and other indexes remain unchanged, the current blood pump adjusting parameters "hold the current parameters", and at the same time the remote service platform 21 can notify the carrier of such information as "the blood pump 30 operates normally and has a good assisting effect" by means of a short message, telephone or e-mail via the local processing terminal 10. However, if the currently collected heart rate of the carrier is 110 times/minute, and other indexes all change to different extents, it is needed to increase the assisted flow of the blood pump 30, then the remote service platform 21 notifies the carrier of such information as "it is needed to increase the assisted flow due to a change in state, please adjust the rotation speed up to 2500 rpm" by means of a short message, telephone or e-mail via the local processing terminal 10. By instructing the carrier to adjust the control driver, or remotely controlling the local processing terminal 10 and adjusting the control driver to adjust the current blood pump rotation speed up to 2500 rpm and the corresponding blood pump assisted flow to 5 L/min, the heart chamber assisting of the carrier can be made better. It should be noted that, "the set adjusting conditions" here can be set as a "function" or "fixed correspondence relation table" according to "clinical test data" or "conventionally set adjusting conditions"; when "the current state parameters (pump voltage, pump current, pump rotation speed, pump flow) and the heart activity indexes (heart rate) of the carrier" are given, consistent "blood pump adjusting parameters" can be given to different carriers. So, it can be seen that, "the set adjusting conditions" are not special conditions given to different carriers but are universally set conditions given according to the "clinical test data" or "conventionally set adjusting conditions". After one or both of the remote processing platform (1) 22 and the remote processing platform (2) 23 has obtained the current blood pump adjusting parameters according to the current state parameters and the heart rate of the carrier and related information in combination with the set adjusting conditions, it uploads them to the remote service platform 21. It should be noted that, according to actual needs, an authority of the current blood pump adjusting parameters obtained by the remote processing platform (1) 22 (or remote processing platform (2) 23) can be set higher than an authority of the current blood pump adjusting parameters obtained by the remote processing platform (2) 23 (or remote processing platform (1) 22). For example, the remote processing platform (1) 22 is a medical institution platform, and the remote processing platform (2) 23 is a manufacture platform. After both the remote processing platform (1) 22 and the remote processing platform (2) 23 receive the current state parameters and the heart activity indexes of the remote carrier via the remote service platform 21, the current blood pump adjusting parameters made by the remote processing platform (1) 22 shall be adopted or accepted in preference to the current blood pump adjusting parameters made by the remote processing platform (2) 23. The remote service platform 21 transmits the blood pump adjusting parameters back to the local processing terminal 10 (specifically by a short message. If the remote transceiver terminal 13 is a smart mobile terminal, e.g., smart phone, and the carrier information is user information collectively registered with or possessed by the local processing terminal 10 and the remote processing terminal 20, the blood pump adjusting parameters can be transmitted back to the local processing terminal 10 also by means of push).

The local processing terminal 10 receives the "blood pump adjusting parameters" from the remote processing terminal 20 via the remote transceiver terminal 13 and transmits the "blood pump adjusting parameters" to the driving module 14. The driving module 14 adjusts the current pump rotation speed according to the blood pump adjusting parameters such as rotation speed. If the rotation speed adjusting parameter is "accelerating the rotation speed by 100 rpm", the driving module 14 increases the rotation speed of the blood pump 30 by 100 rpm.

It can be seen that, the local processing terminal 10 transmits the collected current state parameters of the blood pump 30 and the heart activity indexes to the remote processing terminal 20; the remote processing terminal 20 modifies the current blood pump adjusting parameters according to the current state parameters, the heart activities indexes received from the local processing terminal 10, and the set adjusting conditions; and transmits the modified blood pump adjusting parameters to the local processing terminal 10; and drives and controls the blood pump 30 according to the parameters after the local processing terminal 10 receives the modified drive parameters from the remote processing terminal 20.

Figure 2:
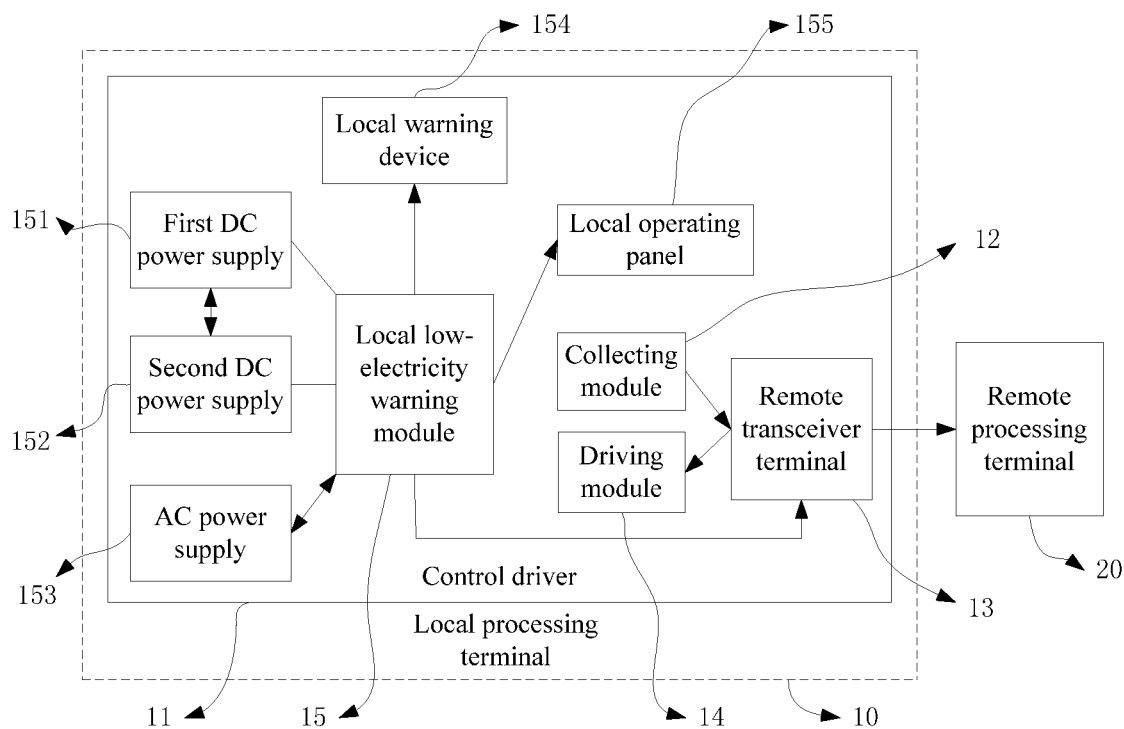
FIG. 2 is a schematic diagram showing components of a blood pump control system comprising electricity monitoring according to an embodiment of the invention.

In order that the state of the blood pump 30 is more safe and reliable in the operation, in an embodiment of the invention, as shown in FIG. 2, the control driver 11 in the local processing terminal 10 is supplied using a 12~18 V DC power supply. In view of the importance of the power energy, a triple redundancy solution is adopted, that is, the control driver 11 is externally connected to a first DC power supply 151, a second DC power supply 152 (i.e., two high-capacity lithium polymer batteries), and an AC power supply 153 (i.e., externally connected to an AC adapter). The two high-capacity lithium polymer batteries have a low-electricity switching function and supply power to the control driver 11 as mutual backup, which sufficiently guarantee reliable power energy in outdoor activities, longer free time and higher quality of life. If the patient is indoors, the control driver 11 can be power supplied by one AC adapter. In order to guarantee safety, even if the control driver 11 is power supplied by the AC adapter, the high-capacity lithium polymer batteries must be provided for preventing situations such as sudden power failure. The AC adapter is not responsible for charging the batteries and the charging the lithium polymer batteries must be performed by a separately configured battery desktop charger. In order to make the monitoring of the power supply more reliable, the local processing terminal 10 further comprises: a local low-electricity warning module 15, a local warning device 154 or a local operating panel 155. A collecting input terminal of the local low-electricity warning module 15 is connected to the first DC power supply 151, the second DC power supply 152 and the AC power supply 153 and collects electricity values of the first DC power supply 151, the second DC power supply 152 and the AC power supply 153 in real time. An output terminal of the local low-electricity warning module 15 is connected to the local warning device 154 or the local operating panel 155. When a total electricity of the first DC power supply 151, the second DC power supply 152 and the AC power supply 153 is less than a minimum electricity value, the local low-electricity warning module 15 generates local low-electricity warning information or a low-electricity warning acknowledgement request, and transmits the local low-electricity warning information to the local warning device 154, and the local warning device 154 uses a buzzer or a photoelectric warning device, or transmits the low-electricity warning acknowledgement request to the local operating panel 155 to wait for an acknowledgement from the carrier; if within a set period, a warning acknowledgement is not received, remote low-electricity warning information is generated and transmitted to the remote processing terminal 20. The local low-electricity warning module 15 can be implemented by an embedded unit integrated on the control driver 11. For example, if the electricity value of the first DC power supply 151 is 10% and the electricity value of the second DC power supply 152 is 80%, and the total electricity value of the first DC power supply 151 and the second DC power supply 152 is less than the set total electricity threshold 95%, then the local low-electricity warning module 15 activates a local buzzer or photoelectric device (local warning device 154) to warn and prompt the carrier. In order to prevent the carrier from not taking notice of the warning information from the prompt from the warning device so as to bring a risk to the carrier, the local low-electricity warning module 15 generates a low-electricity warning acknowledgement request and displays the request by a display screen (self-configured on the control driver 11) and waits for a period of time (e.g., 30 s) for acknowledgement from the user; when the carrier acknowledges the request by the local operating panel 155, the warning is finished. If the carrier does not acknowledge it, that is, if a warning acknowledgement is not received, the local low-electricity warning module 15 generates remote low-electricity warning information which is transmitted to the remote processing terminal 20 via the remote transceiver terminal 13. The local low-electricity warning module 15 can be implemented by an embedded unit integrated on the control driver 11.

Figure 3:
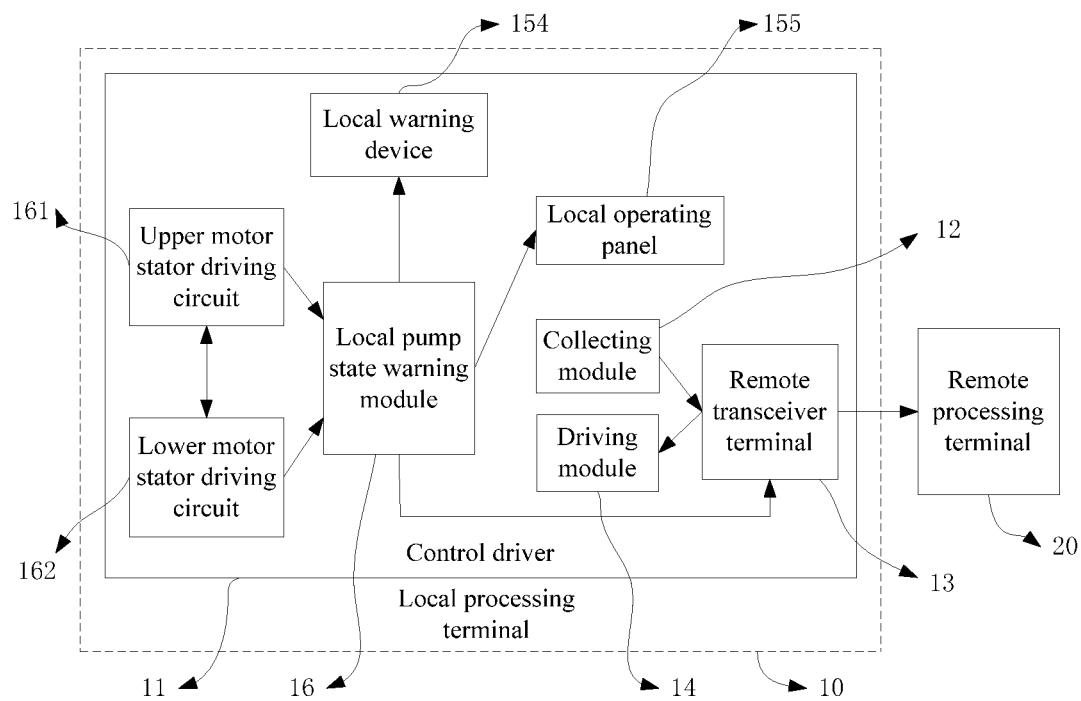
FIG. 3 is a schematic diagram showing components of a blood pump control system comprising motor monitoring according to an embodiment of the invention.

In order to detect a failure of the blood pump 30 in time to thereby guarantee more safe and reliable operations, in an embodiment of the invention, as shown in FIG. 3, when the blood pump 30 uses a double-stator motor (upper motor stator and lower motor stator), the control driver 11 drives the upper motor stator and the lower motor stator respectively by an upper motor stator driving circuit and a lower motor stator driving circuit. In order to guarantee that the upper motor stator and the lower motor stator operate normally, the local processing terminal 10 further comprises: a local pump state warning module 16, a local warning device 154 or a local operating panel 155. A collecting input terminal of the local pump state warning module 16 is connected to the upper motor stator driving circuit 161 and the lower motor stator driving circuit 162 and collects a first motor feedback signal and a second motor feedback signal in real time. An output terminal of the local pump state warning module 16 is connected to the local warning device 154 or the local operating panel 155. When the first motor feedback signal (i.e., upper motor feedback signal) or the second motor feedback signal (i.e., lower motor feedback signal) is abnormal, for example, when the first motor feedback signal is no signal or the second motor feedback signal is no signal, the local pump state warning module 16 generates local pump state warning information or a pump state warning acknowledgement request, and transmits the local pump state warning information to the local warning device 154, and the local warning device 154 uses a buzzer or a photoelectric warning device, or transmits the pump state warning acknowledgement request to the local operating panel 155 to wait for an acknowledgement from the carrier; if within a set period, a warning acknowledgement is not received, remote pump state warning information is generated and transmitted to the remote processing terminal 20. The local pump state warning module 16 can be implemented by an embedded unit integrated on the control driver 11. For example, when the upper motor stator stops, the first motor feedback signal (i.e., upper motor feedback signal) is null, then the local pump state warning module 16 activates a local buzzer or photoelectric device (local warning device 154) to warn and prompt the carrier. In order to prevent the carrier from not taking notice of the warning information from the prompt from the warning device so as to bring a risk to the carrier, the local pump state warning module 16 generates a pump state warning acknowledgement request and displays the request by a display screen (self-configured on the control driver 11) and waits for a period of time (e.g., 30 s) for acknowledgement from the user. When the carrier acknowledges the request by the local operating panel 155, the warning is finished. If the carrier does not acknowledge it, that is, if a warning acknowledgement is not received, the local pump state warning module 16 generates remote pump state warning information which is transmitted to the remote processing terminal 20 via the remote transceiver terminal 13. The local pump state warning module 16 can be implemented by an embedded unit integrated on the control driver 11.

Figure 4:
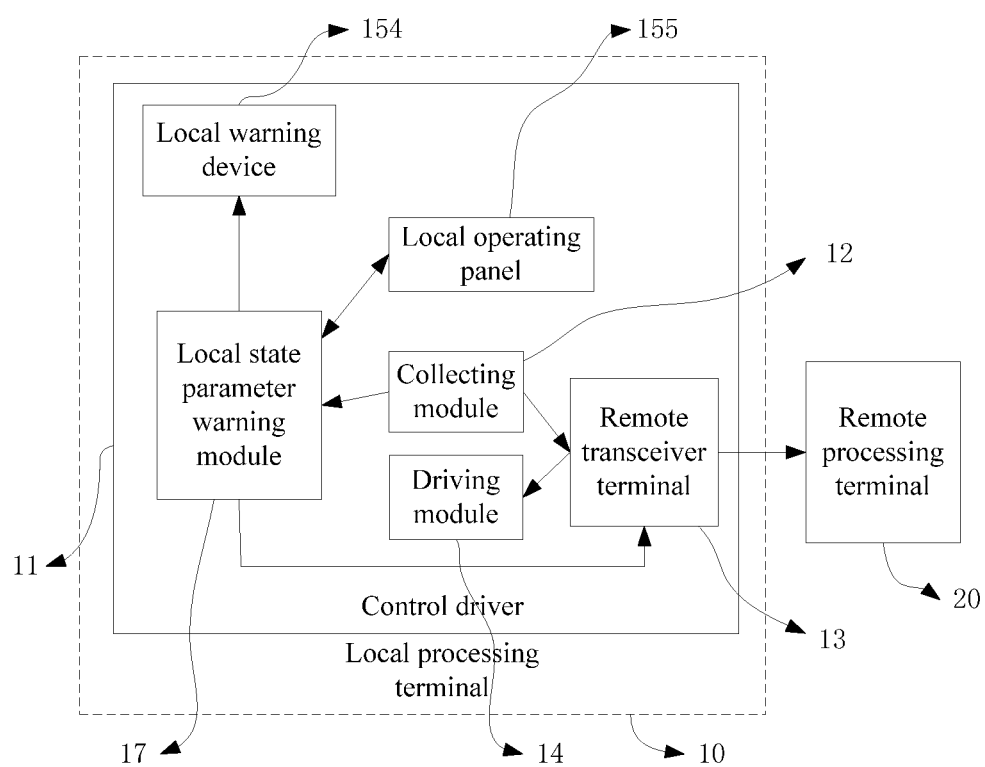
FIG. 4 is a schematic diagram showing components of a blood pump control system comprising current state parameter monitoring according to an embodiment of the invention.

In order to monitor the physical condition of the carrier in real time, in an embodiment of the invention, as shown in FIG. 4, the local processing terminal 10 further comprises: a local state parameter warning module 17, a local warning device 154 or a local operating panel 155. A collecting input terminal of the local state parameter warning module 17 is connected to the collecting module 12 and obtains the pump voltage, pump current, pump rotation speed, pump flow or heart rate from the collecting module 12. An output terminal of the local state parameter warning module 17 is connected to the local warning device 154 or the local operating panel 155. When the pump voltage, pump current, pump rotation speed, pump flow or heart rate is abnormal, for example, when the pump flow is less than a flow warning threshold, the local state parameter warning module 17 generates local state parameter warning information or a state parameter warning acknowledgement request, and transmits the local state parameter warning information to the local warning device 154, and the local warning device 154 uses a buzzer or a photoelectric warning device, or transmits the state parameter warning acknowledgement request to the local operating panel 155 to wait for an acknowledgement from the carrier; if within a set period, a warning acknowledgement is not received, remote state parameter warning information is generated and transmitted to the remote processing terminal 20. The local state parameter warning module 17 can be implemented by an embedded unit integrated on the control driver 11. For example, when the pump flow is less than the flow warning threshold, the local state parameter warning module 17 activates a local buzzer or photoelectric device (local warning device 154) to warn and prompt the carrier. In order to prevent the carrier from not taking notice of the warning information from the prompt from the warning device so as to bring a risk to the carrier, the local state parameter warning module 17 generates a state parameter warning acknowledgement request and displays the request by a display screen (self-configured on the control driver 11) and waits for a period of time (e.g., 30 s) for acknowledgement from the user; when the carrier acknowledges the request by the local operating panel 155, the warning is finished. If the carrier does not acknowledge it, that is, if a warning acknowledgement is not received, the local state parameter warning module 17 generates remote state parameter warning information which is transmitted to the remote processing terminal 20 via the remote transceiver terminal 13. The local state parameter warning module 17 can be implemented by an embedded unit integrated on the control driver 11.

It should be noted that, in order to discriminate the local low-electricity warning information, the local pump state warning information and the local state parameter warning information, different warning modes can be set for different warning information, e.g., different sounds or different photoelectric flickering modes. In order to facilitate identification by the carrier, the warning can be made also by playing a voice, e.g., the "local low-electricity warning information" can be promoted by playing voice "insufficient electricity" by the warning device. Different warning information corresponds to a different voice, and the voice playing function can be implemented by means of database and the set association.

Figure 5:
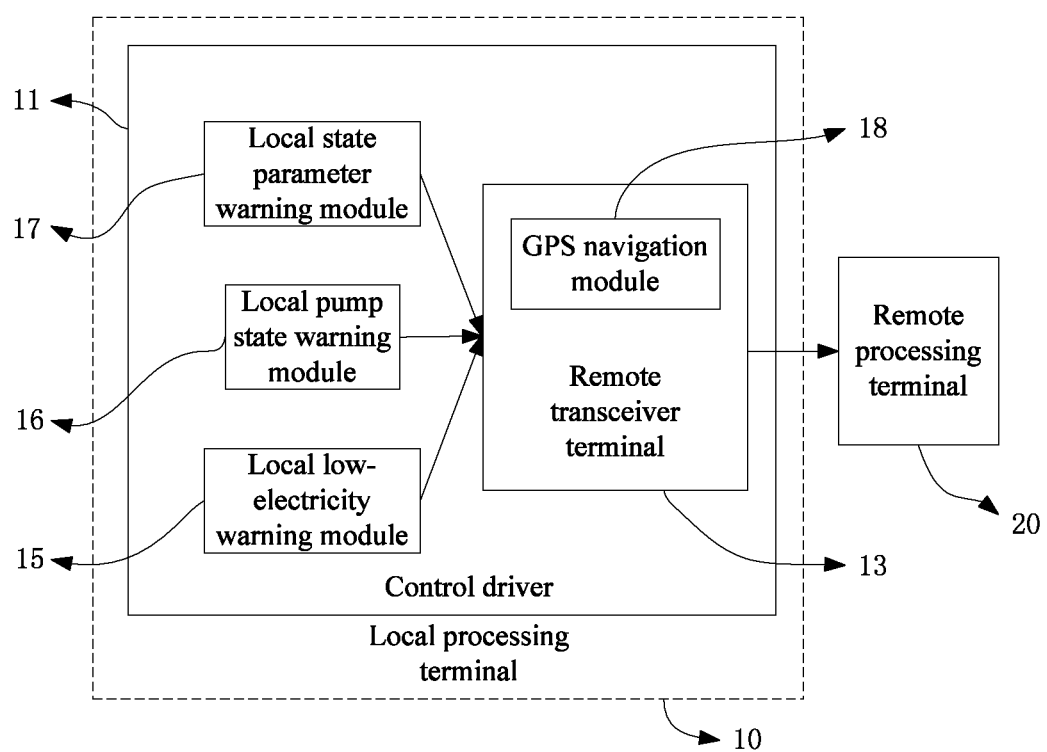
FIG. 5 is a schematic diagram showing components of a blood pump control system comprising a GPS navigation module according to an embodiment of the invention.

In order that the remote processing terminal 20 can learn the current position of the carrier at any time when the control driver 11 transmits the warning information out to the remote processing terminal 20, as shown in FIG. 5, the remote transceiver terminal 13 further comprises a GPS navigation module 18 configured to obtain the current position navigation information if the remote low-electricity warning information, the remote pump state warning information or the remote state parameter warning information exists. Meanwhile, in order to provide rescue to the carrier timely, when the remote transceiver terminal 13 receives "the remote low-electricity warning information, the remote pump state warning information or the remote state parameter warning information", a call request can be made to a first emergency call number by a local number. If the first emergency call number does not reply within the set period, a call request is made to the second emergency call number. Any of the first emergency call number and the second emergency call number can be preset as a rescue station number (the first emergency call number or the second emergency call number was pre-stored in the transceiver terminal 13).

Meanwhile, the information can also be transmitted by means of a short message. The remote transceiver terminal 13 generates low-electricity warning instant information, pump state warning instant information or state parameter warning instant information according to the remote low-electricity warning information, the remote pump state warning information or the remote state parameter warning information, when receiving the remote low-electricity warning information, the remote pump state warning information or the remote state parameter warning information, and the instant information shall comprise unique identification information of the carrier. The low-electricity warning instant information, the pump state warning instant information or the state parameter warning instant information is transmitted to a first emergency call number via a local number. The low-electricity warning instant information, the pump state warning instant information or the state parameter warning instant information is transmitted to a second emergency call number if a reply to the instant information is not received within a set period. Alternatively, the remote transceiver terminal 13 generates low-electricity warning instant information, pump state warning instant information or state parameter warning instant information according to the remote low-electricity warning information, the remote pump state warning information or the remote state parameter warning information and the position navigation information, when receiving the remote low-electricity warning information, the remote pump state warning information or the remote state parameter warning information; transmits the low-electricity warning instant information, the pump state warning instant information or the state parameter warning instant information to a first emergency call number via a local number, and transmits the low-electricity warning instant information, the pump state warning instant information or the state parameter warning instant information to a second emergency call number if a reply to the instant information is not received within a set period. Therefore, the current position of the carrier can be determined more accurately to facilitate rescue to the carrier.

Figure 6:
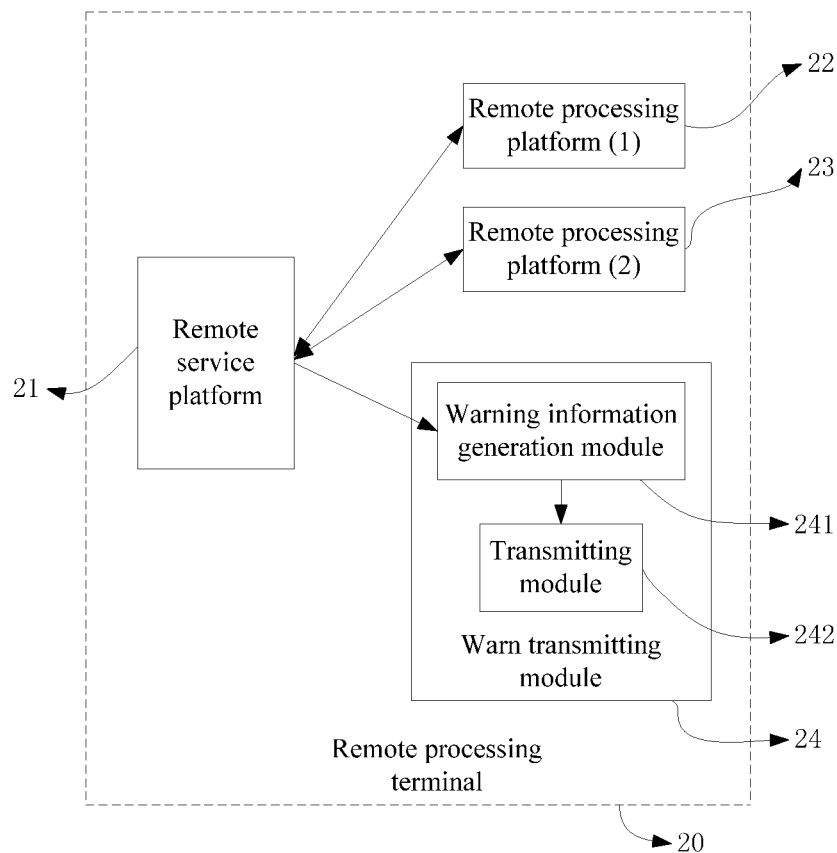
FIG. 6 is a schematic diagram showing components of a remote processing terminal of a blood pump control system according to an embodiment of the invention.

In order that the warning information transmitted to the remote processing terminal 20 can be transmitted out at any time, as shown in FIG. 6, the remote processing terminal 20 further comprises a warning transmitting module 24. The module 24 comprises a warning information generation module 241 and a transmitting module 242. If the remote processing platform (1) 22 or the remote processing platform (2) 23 is an intelligent terminal, that is, if the platform can process a push message, the warning information generation module generates low-electricity warning push information, pump state warning push information or state parameter warning push information according to the low-electricity warning information and its corresponding position navigation information, the pump state warning information and its corresponding position navigation information or the state parameter warning information and its corresponding position navigation information. The push information is transmitted to the "transmitting module 242" that transmits an instant message to a first emergency number or pushes the information to a first emergency account. If a reply from the first emergency call number is not received within a set period, the transmitting module 242 transmits an instant message to a second emergency number or pushes the information to a second emergency account. It can be seen that, in order to realize the above information push function, it is needed to store in the remote service platform 21, the remote processing platform (1) 22 and the remote processing platform (2) 23, account information of the remote processing platform (1) 22 and the remote processing platform (2) 23 and a call correspondence relationship between the carrier and the remote processing platform (1) 22 or the remote processing platform (2) 23, for facilitating invocation while pushing the information.

Figure 7:
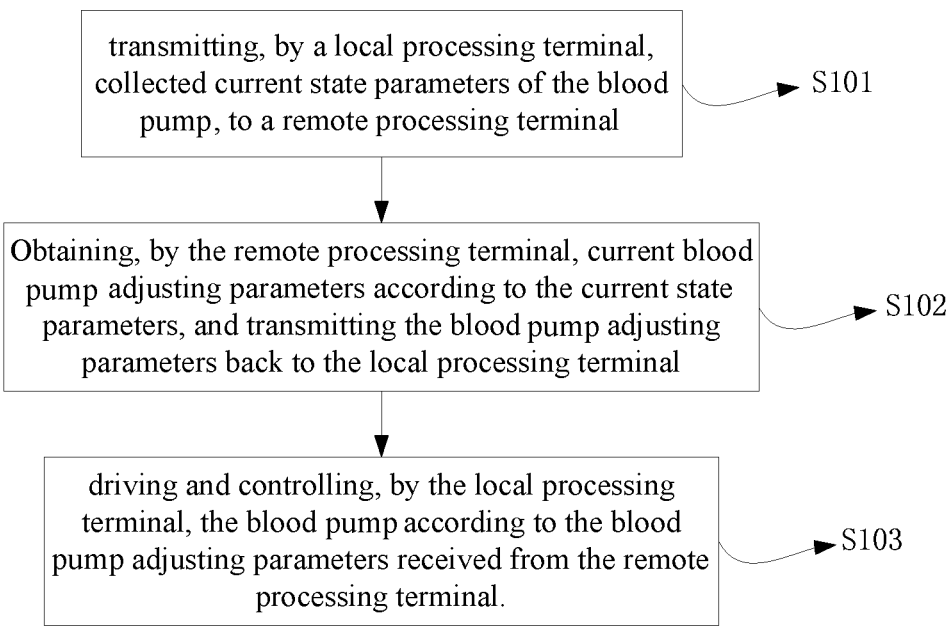
FIG. 7 is a diagram showing steps of a blood pump control method according to an embodiment of the invention.

As shown in FIG. 7, the invention also provides a blood pump control method comprising:

a step S101 of transmitting, by a local processing terminal 10, collected current state parameters of the blood pump 30 and heart activity indexes, to a remote processing terminal 20;

a step S102 of obtaining, by the remote processing terminal 20, current blood pump adjusting parameters, according to the current state parameters and the heart activity indexes received from the local processing terminal 10, and the set adjusting conditions; and transmitting the blood pump adjusting parameters back to the local processing terminal 10;

a step S103 of driving and controlling, by the local processing terminal 10, the blood pump 30 according to the blood pump adjusting parameters received from the remote processing terminal 20.

Figure 8:
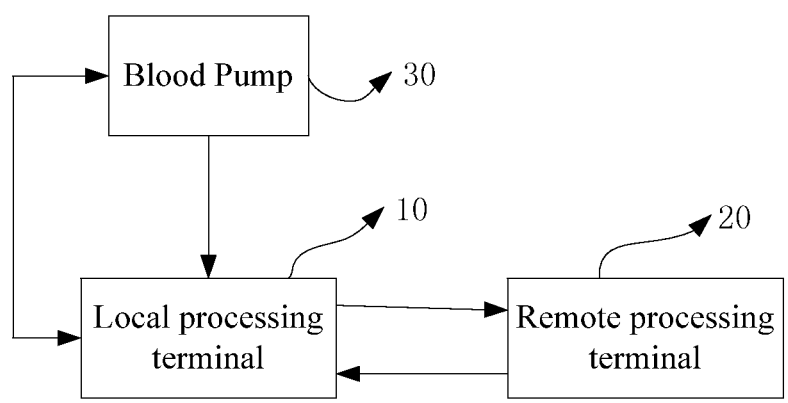
FIG. 8 is a schematic diagram showing components of a blood pump system according to an embodiment of the invention.

As shown in FIG. 8, an embodiment of the invention also provides a blood pump system comprising a blood pump 30 and the above-mentioned blood pump control system (comprising the local processing terminal 10 and the remote processing terminal 20). The blood pump 30 is an arbitrary blood pump, preferably a contactless suspending rotary blood pump, e.g., magnetic fluid double-suspending centrifugal rotary blood pump, axial flow rotary blood pump.

The above merely are some embodiments of the invention. Those skilled in the art could make several variants and modifications without departing from the inventive concept of the invention, and all these variants and modifications fall within the scope of protection of the invention.

The invention claimed is:
1. A blood pump control system, comprising:
a local processing terminal;
a remote processing terminal;
the local processing terminal being configured to transmit to the remote processing terminal, collected current state parameters of a blood pump and heart activity indexes, and to drive and control the blood pump according to blood pump adjusting parameters received from the remote processing terminal;
the remote processing terminal being configured to obtain current blood pump adjusting parameters according to: the current state parameters and the heart activity indexes received from the local processing terminal; and set adjusting conditions that were set according to at least one of clinical test data or conventionally set adjusting conditions;

said remote processing terminal additionally configured to wirelessly transmit the obtained blood pump adjusting parameters back to the local processing terminal; and said local processing terminal configured to drive and control the blood pump according to obtained blood pump adjusting parameters transmitted wirelessly from the remote processing terminal to the local processing terminal.

2. The blood pump control system of claim 1, wherein:

the local processing terminal includes a collecting module, a remote transmitting terminal and a driving module;

the collecting module being configured to collect blood pump state parameters and heart activity indexes of a carrier;

the remote transmitting terminal being configured to transmit the blood pump state parameters and the heart activity indexes of the carrier to the remote processing terminal in a wireless or wired communication mode;

the collecting module being connected to the remote transmitting terminal via USB and/or a short distance wireless communication interface; and the driving module being configured to drive and control the blood pump according to the blood pump adjusting parameters received from the remote processing terminal.

3. The blood pump control system of claim 2, wherein:

the local processing terminal is supplied with power by a power supply including a direct current (DC) power supply and/or an alternating current (AC) power supply.

4. The blood pump control system of claim 3, wherein the local processing terminal further includes at least one of the following:

a local low-electricity warning module configured to generate local low-electricity warning information or a low-electricity warning acknowledgement request if a total electricity or voltage value of the DC power supply and the AC power supply is lower than a set electricity or voltage value;

a local pump state warning module configured to generate local pump state warning information or a pump state warning acknowledgement request if a first motor feedback signal or a second motor feedback signal of the blood pump is an abnormal signal; and a local state parameter warning module configured to generate local state parameter warning information or a state parameter warning acknowledgement request if any value of pump voltage, pump current, pump rotation speed, pump flow or heart rate is abnormal.

5. The blood pump control system of claim 4, wherein:

the local processing terminal further includes a warning device configured to output the local low-electricity warning information, the local pump state warning information or the local state parameter warning information.

6. The blood pump control system of claim 4, wherein:

the local low-electricity warning module, the local pump state warning module or the local state parameter warning module is further configured to generate remote low-electricity warning information, remote pump state warning information or remote state parameter warning information if a warning acknowledgement is not received within a set period.

7. The blood pump control system of claim 6, wherein:

the remote transmitting terminal is further configured to transmit the remote low-electricity warning information, the remote pump state warning information or the remote state parameter warning information to the remote processing terminal in a wireless or wired communication mode.

8. The blood pump control system of claim 7, wherein:

the remote transmitting terminal further includes a GPS navigation module configured to obtain current position navigation information if the remote low-electricity warning information, the remote pump state warning information or the remote state parameter warning information is received.

9. The blood pump control system of claim 6, wherein:

the remote transmitting terminal is further configured to make a call request to a first emergency call number via a local number, if the remote low-electricity warning information, the remote pump state warning information or the remote state parameter warning information is received, and to make a call request to a second emergency call number if the first emergency call number does not reply within a set period.

10. The blood pump control system of claim 6, wherein the remote transmitting terminal is further configured to:

generate low-electricity warning instant information, pump state warning instant information or state parameter warning instant information according to the remote low-electricity warning information, the remote pump state warning information or the remote state parameter warning information, if the remote low-electricity warning information, the remote pump state warning information or the remote state parameter warning information is received;

transmit the low-electricity warning instant information, the pump state warning instant information or the state parameter warning instant information to a first emergency call number via a local number; and transmit the low-electricity warning instant information, the pump state warning instant information or the state parameter warning instant information to a second emergency call number if a reply to the instant information is not received within a set period.

11. The blood pump control system of claim 8, wherein the remote transmitting terminal is further configured to:

generate low-electricity warning instant information, pump state warning instant information or state parameter warning instant information according to the remote low-electricity warning information, the remote pump state warning information or the remote state parameter warning information and the position navigation information, if the remote low-electricity warning information, the remote pump state warning information or the remote state parameter warning information is received;

transmit the low-electricity warning instant information, the pump state warning instant information or the state parameter warning instant information to a first emergency call number via a local number; and transmit the low-electricity warning instant information, the pump state warning instant information or the state parameter warning instant information to a second emergency call number if a reply to the instant information is not received within a set period.

12. The blood pump control system of claim 8, wherein:

the remote processing terminal includes a remote service platform and a remote processing platform;

the remote service platform being configured to receive the current pump voltage, pump current, pump rotation speed, pump flow, heart rate from the local processing terminal, and to transmit the blood pump adjusting parameters obtained by the remote processing platform back to the local processing terminal; and the remote processing platform being configured to obtain current blood pump adjusting parameters according to the current pump voltage, pump current, pump rotation speed, pump flow, heart rate, history heart activity indexes of the patient, and the set adjusting conditions.

13. The blood pump control system of claim 12, wherein:
the remote processing platform includes a first remote processing platform and a second remote processing platform;
an authority of the current blood pump adjusting parameters obtained by the first remote processing platform is higher than an authority of the current blood pump adjusting parameters obtained by the second remote processing platform.

14. The blood pump control system of claim 12, wherein:
the remote processing terminal further includes a warning transmitting module configured to generate low-electricity warning push information, pump state warning push information or state parameter warning push information according to the low-electricity warning information and its corresponding position navigation information, the pump state warning information and its corresponding position navigation information or the state parameter warning information and its corresponding position navigation information.

15. The blood pump control system of claim 14, wherein:
the warning transmitting module is further configured to transmit an instant message to a first emergency number according to the remote low-electricity warning push information, the remote pump state warning push information or the remote state parameter warning push information, or push the information to a first emergency account if the remote low-electricity warning push information, the remote pump state warning push information or the remote state parameter warning push information is received, and to transmit an instant message to a second emergency number or push the information to a second emergency account if a reply from the first emergency call number is not received within a set period.

16. The blood pump control system of claim 2, wherein:
the local processing terminal further includes a remote receiving terminal configured to receive the current blood pump adjusting parameters from the remote processing terminal in a wireless or wired communication mode.

17. A blood pump control method comprising:
transmitting, by a local processing terminal, collected current state parameters of a blood pump and heart activity indexes, to a remote processing terminal;
obtaining, by the remote processing terminal, current blood pump adjusting parameters, according to: the current state parameters, and the heart activity indexes received from the local processing terminal; and set adjusting conditions that were set according to at least one of clinical test data or conventionally set adjusting conditions;
wirelessly transmitting, by the remote processing terminal, the obtained blood pump adjusting parameters back to the local processing terminal; and
driving and controlling, by the local processing terminal, the blood pump according to the obtained blood pump adjusting parameters received wirelessly from the remote processing terminal.

18. A blood pump system comprising:
a blood pump; and
a blood pump control system including:
a local processing terminal;
a remote processing terminal;
the local processing terminal being configured to transmit to the remote processing terminal, collected current state parameters of a blood pump and heart activity indexes, and to drive and control the blood pump according to blood pump adjusting parameters received from the remote processing terminal; and
the remote processing terminal being configured to obtain current blood pump adjusting parameters according to: the current state parameters and the heart activity indexes received from the local processing terminal; and set adjusting conditions;
said remote processing terminal additionally configured to transmit the obtained blood pump adjusting parameters back to the local processing terminal;
wherein the local processing terminal is configured to drive and control the blood pump according to obtained blood pump adjusting parameters transmitted wirelessly from the remote processing terminal to the local processing terminal.

19. The blood pump system of claim 18, wherein the blood pump is a suspending rotary blood pump.

* * * * *